US00PP24523P3

(12) United States Plant Patent
Madsen

(10) Patent No.: US PP24,523 P3
(45) Date of Patent: Jun. 3, 2014

(54) ***CAMPANULA* PLANT NAMED 'PKM01'**

(50) Latin Name: ***Campanula* sp.**
Varietal Denomination: PKM01

(75) Inventor: Christian Hald Madsen, Korsor (DK)

(73) Assignee: Gartneriet PKM A/S, Odense N (DK)

( * ) Notice: Subject to any disclaimer, the term of this patent is extended or adjusted under 35 U.S.C. 154(b) by 78 days.

(21) Appl. No.: 13/507,741

(22) Filed: Jul. 25, 2012

(65) Prior Publication Data

US 2014/0033387 P1 Jan. 30, 2014

(51) Int. Cl.
*A01H 5/00* (2006.01)

(52) U.S. Cl.
USPC ..... Plt./414

(58) Field of Classification Search
USPC ..... Plt./414
See application file for complete search history.

*Primary Examiner* — Susan McCormick Ewoldt
(74) *Attorney, Agent, or Firm* — Foley & Lardner LLP

(57) ABSTRACT

A new and distinct cultivar of *Campanula* plant named 'PKM01', characterized by its vigorous growth habit, upright violet flowers, and characteristic linear leaves.

6 Drawing Sheets

Latin name of genus and species of the plant claimed: *Campanula* sp.

Variety denomination: 'PKM01'.

BACKGROUND OF THE INVENTION

The present invention relates to a new and distinct cultivar of *Campanula* plant, botanically known as *Campanula* sp., commonly known as Bellflower, and hereinafter referred to by the name 'PKM01'.

The new *Campanula*, 'PKM01', is a product of a planned breeding program conducted by the inventor, Christian Hald Madsen, in Søhus, Denmark. The new *Campanula* cultivar originated from a planned cross made in July 2007 by the inventor. The cross was made in an insect proof house equipped with bumble bees and around 50 different species of *Campanula* (all PKM property). The seeds were harvested on *Campanula rotundifolia* and the offspring differed significantly from the female parent indicating an interspecific cross. The Inventor selected the new *Campanula* cultivar from the progeny of the above crossing in September 2008 on the basis of its compact and freely flowering habit.

The female or seed parent is an unnamed proprietary selection of *Campanula rotundifolia*. The male or pollen parent is an unnamed proprietary selection of *Campanula* sp.

Asexual reproduction of the new *Campanula* cultivar by terminal cuttings has demonstrated that the combination of characteristics as herein disclosed for the new cultivar are firmly fixed and retained through successive generations of asexual reproduction. The new cultivar reproduces true-to-type.

SUMMARY OF THE INVENTION

The following traits have been repeatedly observed and are determined to be the unique characteristics of 'PKM01'. These characteristics in combination distinguish 'PKM01' as a new and distinct cultivar:

1. Upright plant habit with stiff, upright stems;
2. Bushy and globular plant form;

3. Vigorous growth habit, with less need for chemical growth retardation;
4. Wide, violet flowers with wide and long petals;
5. Linear leaves; and
6. No need for vernalization.

Plants of the instant cultivar 'PKM01' can be compared to plants of the most similar commercial cultivar, the *Campanula portenschlagiana Schult.* designated 'PMKp05' (patented, U.S. Plant Pat. No. 17,188). Plants of the new *Campanula* sp. 'PKM01' differ from plants of *Campanula portenschlagiana Schult.* 'PKMp05', primarily in the following characteristic:

1. Plants of 'PKM01' have lighter violet flowers than plants of 'PKMp05'.
2. Plants of 'PKM01' have a linear upper leaves whereas plants of 'PKMp05' have cordate leaves.
3. Plants of 'PKM01' have differing upper and lower leaf shapes whereas plants of 'PKMp05' have identical upper and lower leaf shapes.

BRIEF DESCRIPTION OF THE PHOTOGRAPHS

The accompanying colored photographs illustrate the overall appearance of the new *Campanula* 'PKM01', showing the colors as true as it is reasonably possible to obtain in colored reproductions of this type. Colors in the photographs may differ slightly from the color values cited in the detailed botanical description, which more accurately describe the actual colors of 'PKM01'.

DETAILED BOTANICAL DESCRIPTION

Figure 1:
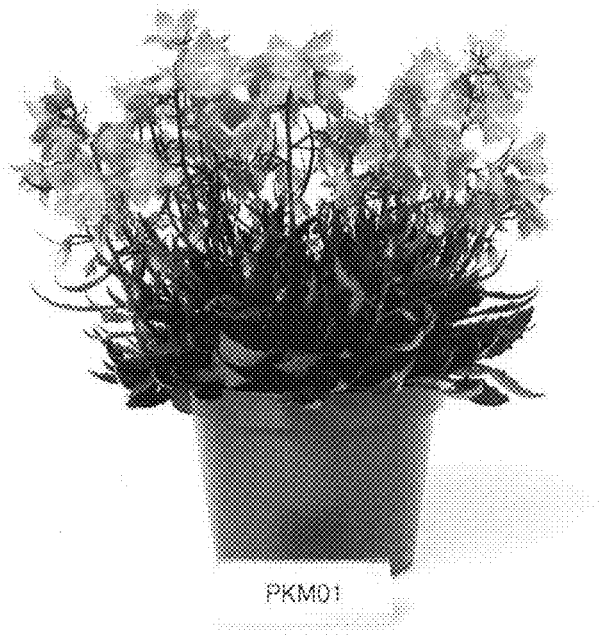
FIG. 1 shows a side perspective view of a typical flowering plant of 'PKM01'.
Figure 2:
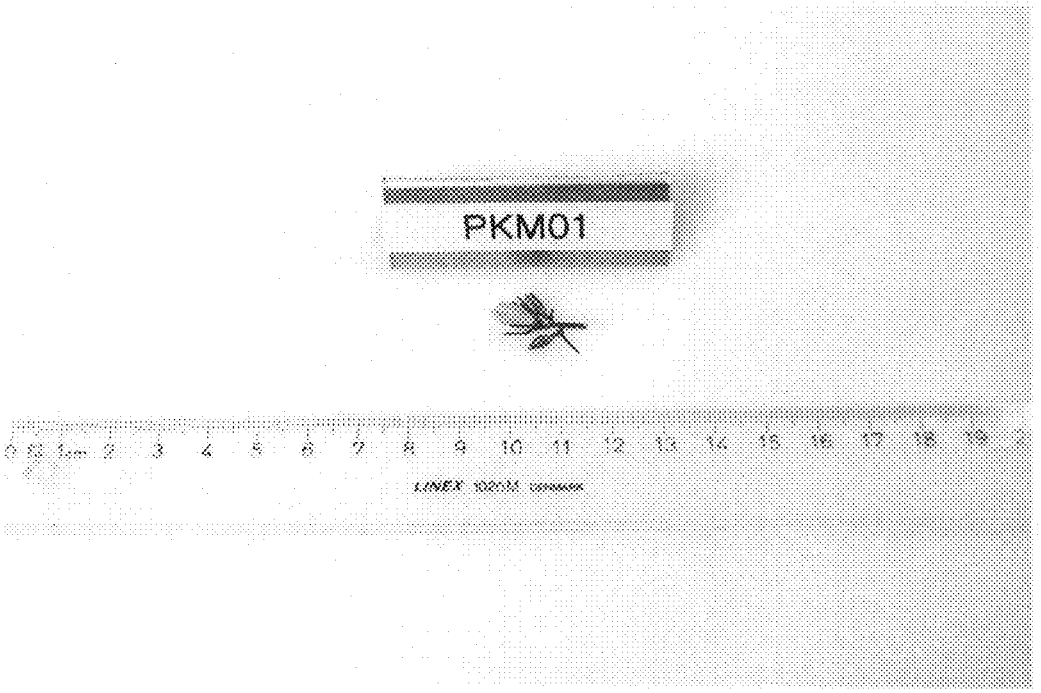
FIG. 2 shows a close-up view of a typical flower bud of 'PKM01'.
Figure 3:
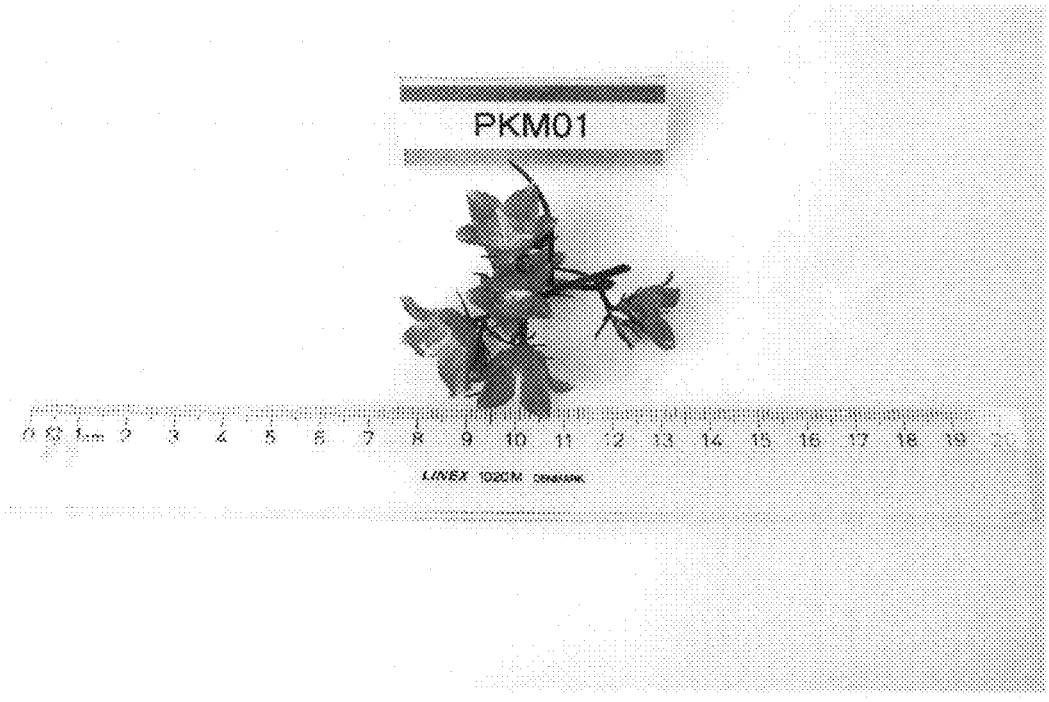
FIG. 3 shows a close-up view of a typical inflorescence of 'PKM01'.
Figure 4:
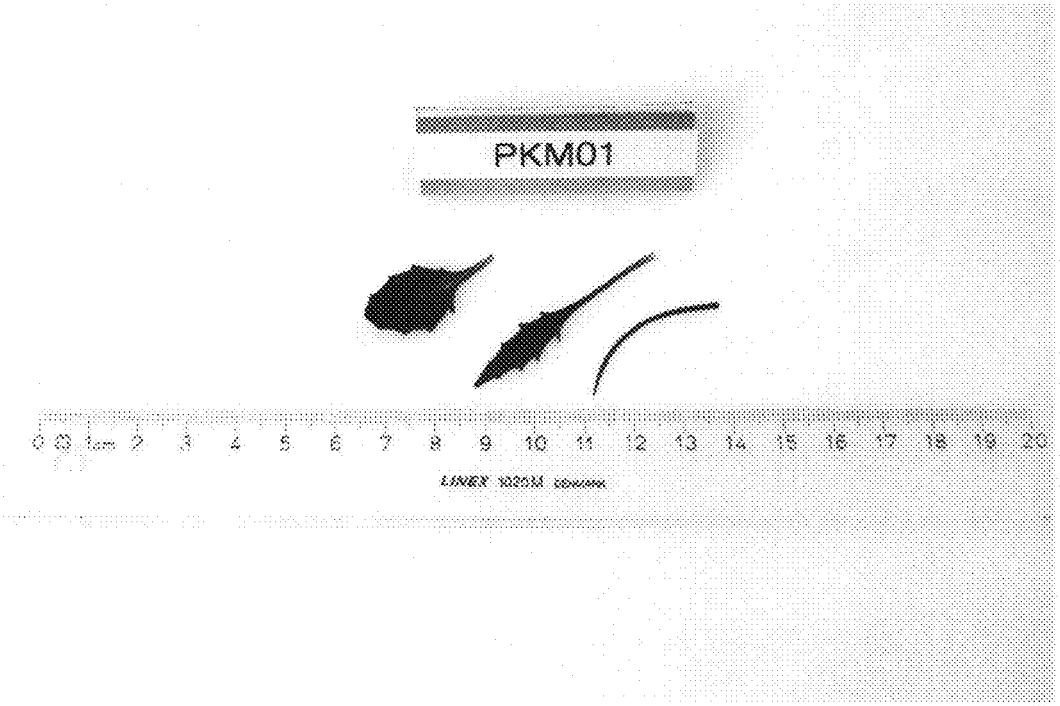
FIG. 4 shows a close-up view of typical leaves of 'PKM01'.
Figure 5:
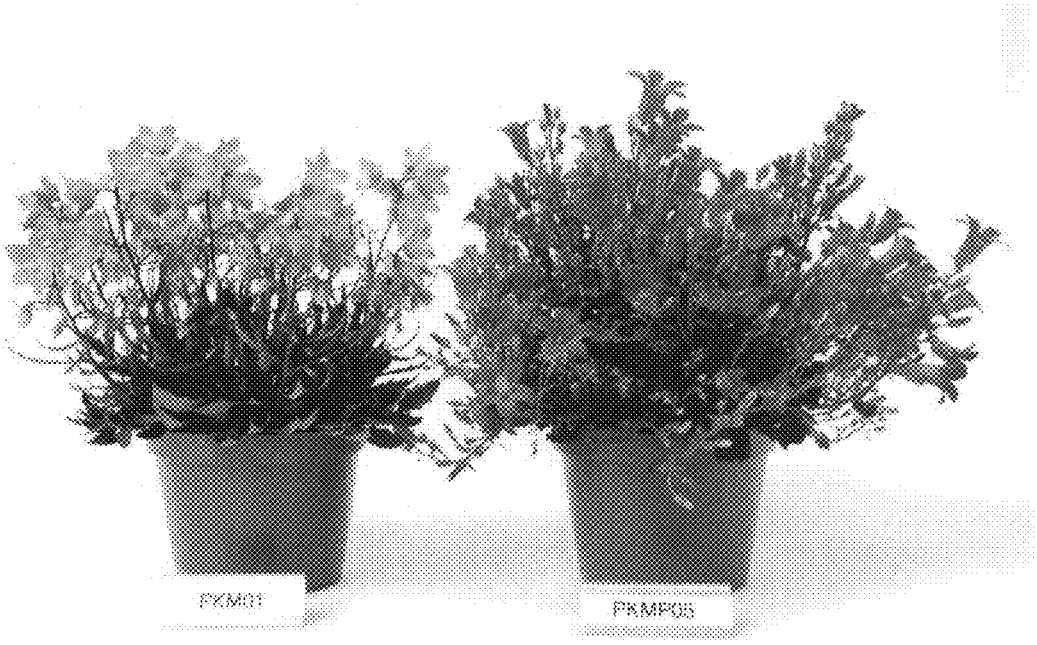
FIG. 5 shows a side view of a typical flowering plant of 'PKM01' compared with a typical flowering plant of 'PKMp05'.
Figure 6:
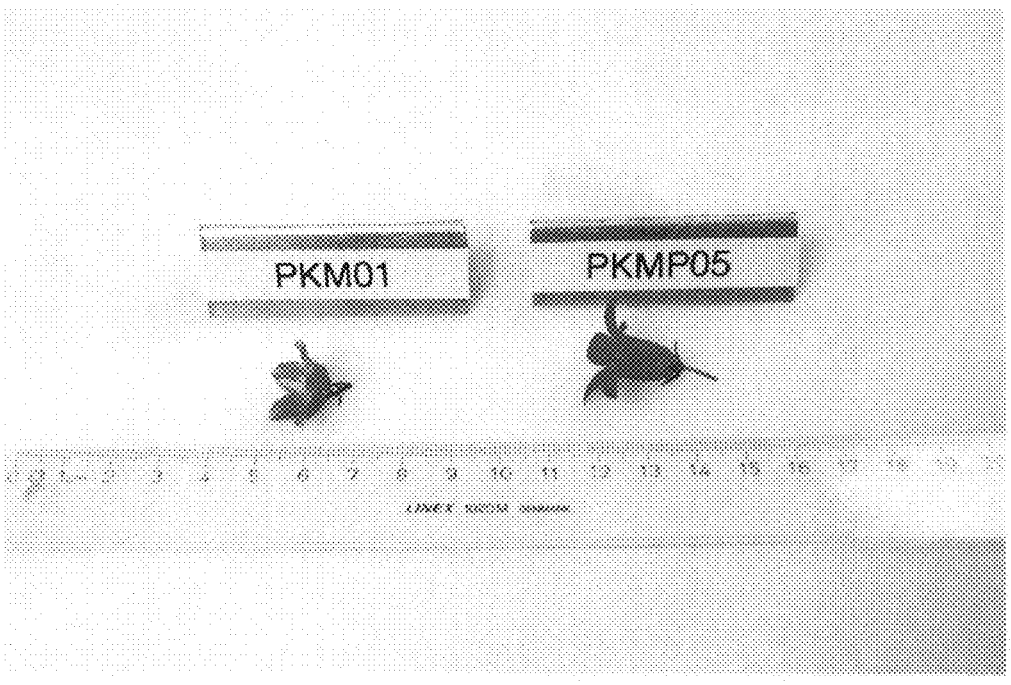
FIG. 6 shows a close-up side view of a typical flower of 'PKM01' compared with a typical flower of 'PKMp05'.

The new *Campanula* 'PKM01' has not been observed under all possible environmental conditions. The phenotype of the new cultivar may vary with variations in environment such as temperature, light intensity, day length, and fertility level without any variance in genotype.

The aforementioned photographs, together with the following observations, measurements and values describe plants of the new *Campanula* 'PKM01' as grown under greenhouse conditions which closely approximate those generally used in commercial practice where day temperatures in the greenhouse range from 18-22° C. and night temperatures are 16° C. Ambient light levels used while growing plants of 'PKM01' are 100 $Wm^2$. Plants of 'PKM01' are grown with long day photoperiodic treatment. Propagation and young plants are exposed to 10 hour short photoperiodic treatments. No growth retardants used.

The age of the 'PKM01' plants described is about 14 weeks after cutting and grown in 10.5 cm pots. Color references are made to The Royal Horticultural Society Colour Chart (R.H.S.), $5^{th}$ edition, except where general colors of ordinary significance are used.

Classification:

*Botanical.*—*Campanula* sp.

Parentage:

*Female or seed parent.*—Unnamed proprietary selection of *Campanula rotundifolia.*

*Male or pollen parent.*—Unnamed proprietary selection of *Campanula* sp.

Propagation:

*Type cutting.*—Terminal vegetative cuttings.

*Time to initiate roots.*—About 10 to 14 days at 18 to 21° C. in tunnels in a greenhouse.

*Root description.*—Fine, well branched.

Plant description:

*Form.*—Perennial, rosette plant with upright plant habit. Campanulate flowers in racemes. Freely branching with lateral branches forming at every node.

*Crop time.*—After rooting, about 14 weeks are required to produce finished flowering plants in 11 cm pots.

*Vigor.*—Vigorous growth rate.

*Plant height* (*from soil level to top of plant plane*).—About 12 to 15 cm.

*Plant spread* (*width*).—16-19 cm.

Foliage description:

*Basal leaves.*—Arrangement: Single. Overall shape: Oblong, palmate venation. Length: 35-45 mm. Width: 12-18 mm. Margin: Broadly dentate. Texture (both sides): Stiff, glabrous, dull.

*Apical* (*stem*) *leaves.*—Arrangement: Single. Overall shape: Linear. Length: 35-45 mm. Width: 1 mm. Margin: Broadly dentate. Texture (both sides): Stiff, glabrous, dull.

*Basal & apical leaf color.*—Upper surface: Green, RHS N139A. Lower Surface: Green, RHS 137A. Venation: Pattern: Palmate. Upper Surface: Green, RHS 139A. Lower Surface: Green, RHS 137A.

Inflorescence description:

*Flower arrangement and shape.*—Single, upright, campanulate flowers in racemes, flowers with small star-shaped calyx, reflexed.

*Natural flowering season.*—Continuous throughout spring and summer. Season can be extended by long day treatments, no vernalization needed.

*Flower longevity.*—Longevity of individual flowers is highly dependent on temperature and light conditions. Flowers persistent.

*Inflorescence size.*—Length: 6-8 cm. Diameter: 4-5 cm.

*Buds.*—Length: Up to 12 mm. Diameter: Up to 5 mm. Shape: Oblong, ridged. Color: Young buds: RHS N144D to N145D, yellow-green. Mature buds: Base RHS 196A grayed-green, tip 82C violet.

*Flowers.*—Length: 15-17 mm. Diameter: 20-28 mm.

*Acute petal lobes.*—Length (at base): 6-8 mm. Width (at base): 7-9 mm.

*Corolla color.*—Upper and Lower surfaces: RHS N88C, violet, with a distinct groove in center. Margins: RHS 91C, violet-blue.

*Sepals.*—Arrangement: Free. Appearance: Shiny, glabrous. Quantity per flower: 5. Length: 6 mm. Width: 0.5 mm. Overall shape: Linear, reflexed. Color, upper and lower surfaces: Green, RHS 137A.

*Peduncles.*—Length: 10-20 mm. Diameter: 1 mm. Strength: Strong. Color: Green, RHS 139A.

Reproductive organs:

*Androecium.*—Stamen: Quantity: 5, fused until pollen has shed. Anther: Length: 1 mm. Color: Yellow-white 158A. Pollen: Amount: Average. Color: Yellow-white 158A.

*Gynoecium.*—Pistil: Quantity: 1. Length: 17-20 mm. Stigma: Shape: Tripartite. Color: Green-white 157A. Style: Length: 11 mm. Color: 92D, violet-blue. Ovary: Color: 145C, yellow-green.

Weather tolerance: Plants of the new *Campanula* have exhibited good tolerance to drought, rain and wind, with low temperature resistance to −20° C.

I claim:

1. A new and distinct cultivar of *Campanula* plant named 'PKM01', as illustrated and described herein.

* * * * *